US009854958B1

(12) United States Patent
Kukushkin et al.

(10) Patent No.: US 9,854,958 B1
(45) Date of Patent: Jan. 2, 2018

(54) SYSTEM AND METHOD FOR AUTOMATIC PROCESSING OF IMAGES FROM AN AUTONOMOUS ENDOSCOPIC CAPSULE

(71) Applicant: ZEPHYR TECHNOLOGY CO., LIMITED, Hong Kong (HK)

(72) Inventors: Alexander Kukushkin, Moscow (RU); Anastasia Tolstaya, Moscow (RU); Andrey Starikovsky, Moscow (RU); Landysh Gubaidulina, Moscow (RU); Eugene Fedorov, Moscow (RU); Ekaterina Ivanova, Moscow (RU); Igor Zhukov, Moscow (RU); Dmitry Mikhailov, Moscow (RU); Timur Khabibullin, Ufa (RU)

(73) Assignee: Garini Technologies Corporation, Singapore (SG)

(*) Notice: Subject to any disclaimer, the term of this patent is extended or adjusted under 35 U.S.C. 154(b) by 422 days.

(21) Appl. No.: 14/222,637

(22) Filed: Mar. 23, 2014

Related U.S. Application Data

(60) Provisional application No. 61/804,633, filed on Mar. 23, 2013.

(51) Int. Cl.
*A61B 1/00* (2006.01)
*G06T 7/00* (2017.01)
*A61B 1/04* (2006.01)

(52) U.S. Cl.
CPC ........ *A61B 1/00009* (2013.01); *A61B 1/0002* (2013.01); *A61B 1/0005* (2013.01); *A61B 1/041* (2013.01); *G06T 7/0014* (2013.01); *G06T 7/0016* (2013.01); *G06T 2207/10068* (2013.01)

(58) Field of Classification Search
CPC . A61B 1/00009; A61B 1/0002; A61B 1/0005; A61B 1/041; G06T 2007/10068; G06T 7/0012; G06T 7/0014; G06T 7/0016; G06T 2007/100682
See application file for complete search history.

(56) References Cited

U.S. PATENT DOCUMENTS

| 6,709,387 | B1 * | 3/2004 | Glukhovsky | A61B 1/00009 348/399.1 |
| 8,913,807 | B1 * | 12/2014 | Horn | G06K 9/4652 382/128 |
| 2005/0036668 | A1 * | 2/2005 | McLennan | G06K 9/4652 382/128 |
| 2005/0111713 | A1 * | 5/2005 | Jerebko | G06T 7/0012 382/128 |
| 2006/0074275 | A1 * | 4/2006 | Davidson | A61B 1/04 600/160 |
| 2006/0164511 | A1 * | 7/2006 | Krupnik | H04N 7/181 348/65 |
| 2007/0078335 | A1 * | 4/2007 | Horn | A61B 1/04 600/425 |

(Continued)

Primary Examiner — John P Leubecker
(74) Attorney, Agent, or Firm — Bardmesser Law Group

(57) ABSTRACT

A method and system for processing of images from an autonomous endoscopic capsule includes acquiring a video stream from the endoscopic capsule; detecting repeat frames; removing repeat frames from the video stream; adjusting a speed of play back of the video stream based on a value of possibility of skipping significant frames; detecting anomalies; marking frames with anomalies for further review by a physician; and displaying multiple images on a physician's desktop simultaneously in a chronological order in a form of a matrix.

15 Claims, 8 Drawing Sheets

(56) References Cited

U.S. PATENT DOCUMENTS

| | | | | |
|---|---|---|---|---|
| 2008/0024599 A1* | 1/2008 | Hirakawa | ........... | A61B 1/00009 |
| | | | | 348/65 |
| 2008/0051642 A1* | 2/2008 | Krupnik | ............. | A61B 1/00009 |
| | | | | 600/302 |
| 2008/0068454 A1* | 3/2008 | Hirakawa | ........... | A61B 1/00009 |
| | | | | 348/65 |
| 2008/0119691 A1* | 5/2008 | Yagi | .................... | A61B 1/00009 |
| | | | | 600/109 |
| 2008/0232702 A1* | 9/2008 | Kimoto | .................. | A61B 1/041 |
| | | | | 382/232 |
| 2009/0051695 A1* | 2/2009 | Matsuda | .............. | A61B 1/0005 |
| | | | | 345/556 |
| 2010/0150416 A1* | 6/2010 | Kim | ................... | A61B 1/00009 |
| | | | | 382/128 |
| 2011/0007940 A1* | 1/2011 | Hamza | ................. | G06K 9/0063 |
| | | | | 382/103 |
| 2011/0216951 A1* | 9/2011 | Ye | ......................... | G06T 7/0012 |
| | | | | 382/128 |
| 2011/0249952 A1* | 10/2011 | Taniguchi | ........... | A61B 1/00009 |
| | | | | 386/230 |
| 2011/0305377 A1* | 12/2011 | Drozdzal | .............. | G06T 7/0038 |
| | | | | 382/128 |
| 2012/0076372 A1* | 3/2012 | Nishimura | ............... | A61B 1/05 |
| | | | | 382/128 |
| 2012/0316421 A1* | 12/2012 | Kumar | ............... | A61B 1/00009 |
| | | | | 600/407 |
| 2013/0109915 A1* | 5/2013 | Krupnik | ................ | G06T 3/4038 |
| | | | | 600/109 |
| 2013/0121546 A1* | 5/2013 | Guissin | ................ | G06T 7/0012 |
| | | | | 382/128 |
| 2014/0303435 A1* | 10/2014 | Taniguchi | .......... | A61B 1/00009 |
| | | | | 600/103 |

\* cited by examiner

SYSTEM AND METHOD FOR AUTOMATIC PROCESSING OF IMAGES FROM AN AUTONOMOUS ENDOSCOPIC CAPSULE

CROSS-REFERENCE TO RELATED APPLICATIONS

This application is related to U.S. patent application Ser. No. 13/368,636, filed on Feb. 8, 2012, and U.S. patent application Ser. No. 13/707,679, filed on Dec. 7, 2012, the entire contents of which are hereby incorporated by reference.

This application claims priority to U.S. Provisional Patent Application No. 61804633, filed on Mar. 23, 2013.

BACKGROUND OF THE INVENTION

Field of the Invention

The present invention is related to medical endoscopic examination devices, and in particular, to an endoscopic capsule and a method of using it in the gastrointestinal (GI) tract.

Description of the Related Art

Capsule endoscopy is a way to record images of the digestive tract for use in medical examination and diagnosis. A typical capsule is a size and a shape of a large pill and contains a miniature camera. After a patient swallows the capsule, the camera takes pictures as it traverses the inside of the gastrointestinal tract of the patient. The primary use of the capsule endoscopy is to examine areas of the small intestine that cannot be seen by other types of endoscopy, such as colonoscopy or esophagogastroduodenoscopy (EGD).

This type of examination is often done to find sources of bleeding or abdominal pain. The procedure was approved by the U.S. FDA in 2001. Upper endoscopy (EGD) uses a camera attached to a long flexible tube to view the esophagus, the stomach and the beginning of the first part of the small intestine called the duodenum.

A colonoscope, once inserted through the rectum, can view the colon and the distal portion of the small intestine, the terminal ileum. However, these two types of endoscopy cannot visualize the majority of the middle portion of the gastrointestinal tract, the small intestine.

Therefore, capsule endoscopy is useful when disease is suspected in the small intestine and can sometimes diagnose sources of occult bleeding (blood visible microscopically only) or causes of abdominal pain, such as Crohn's disease or peptic ulcers. The capsule endoscopy can use Bluetooth to transfer the captured images.

However, the capsule can be retained in the stomach and/or intestinal tract for a relatively long period of time, as much as 6-12 hours, and waiting for the capsule to reach various areas of interest in the GI tract might require several hours of a physician's time. Also, review of the images requires a high degree of concentration by the physician, if performed in real time. After several hours of work, physician's attention decreases. This increases the possibility of omissions of certain images during the investigation analysis.

It should be noted that typical medical investigations are done because of symptoms experienced by a patient. The findings should be analyzed as soon as possible by the physician. Thus, the analysis should be performed within a short time to reserve time for medical procedures.

Accordingly, there is a need in the art for a system and method for processing of endoscopic capsule images that assists the physician in identifying problem areas, such as polyps, cancerous areas, GI bleeding and the like. It is also desired to improve a usability of an endoscopic capsule in order to reduce examination time.

SUMMARY OF THE INVENTION

The present invention is related to software for analysis of endoscopic capsule images that substantially obviates one or more of the disadvantages of the related art.

A method and system for analysis of images from an endoscopic capsule is provided. The endoscopic capsule is swallowed by a patient, and then moves down the patient's stomach or the GI tract, transmitting a set of images to an external recorder, which stores the images in its memory. After several hours (depending on a particular capsule endoscope used, usually from 6 to 12 hours), capsule endoscope's battery runs down, and the reader is provided to a physician, who moves the images from the reader to a PC, where he can use a special application to analyze them.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and, together with the description, serve to explain the principles of the invention.

DETAILED DESCRIPTION OF THE PREFERRED EMBODIMENTS

Figure 1:
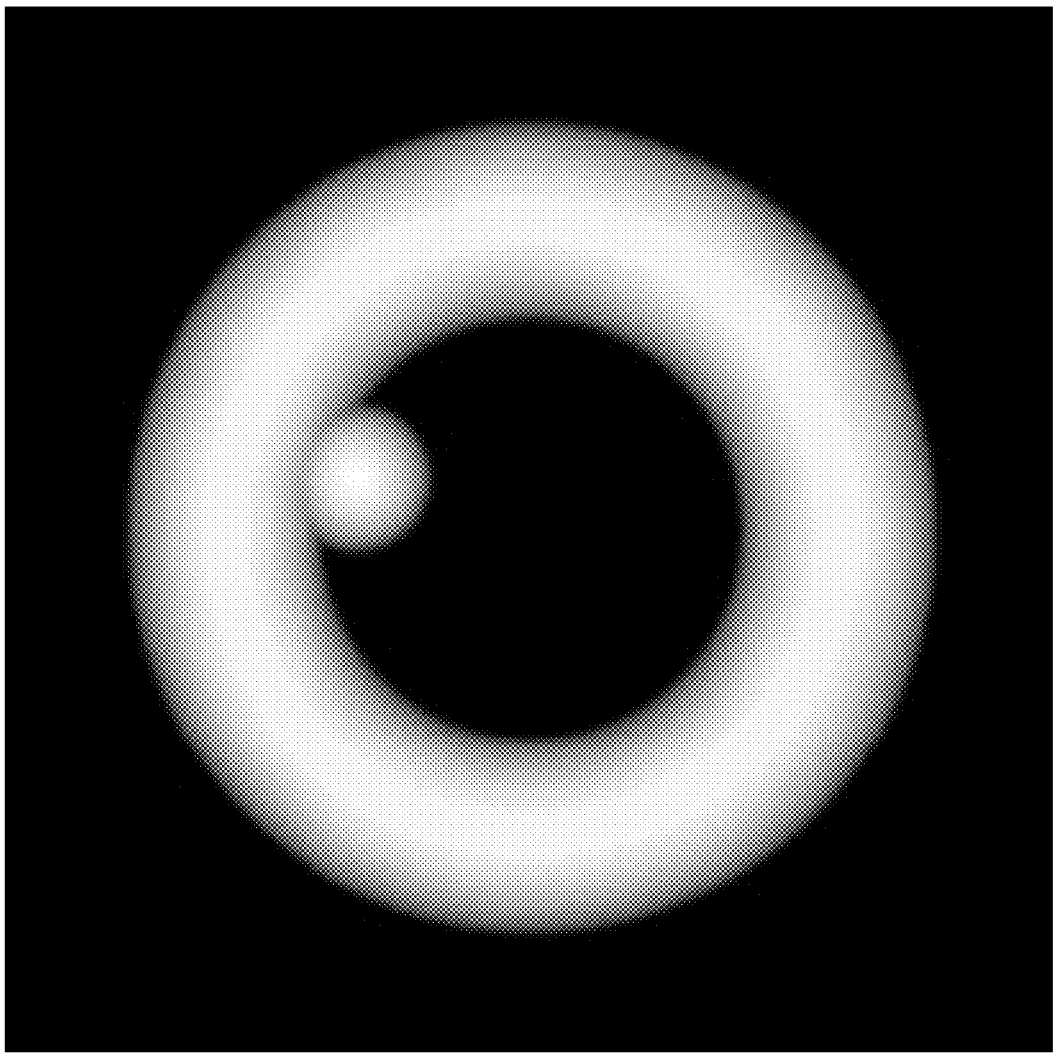
FIG. 1 illustrates an exemplary image of a polyp.
Figure 2:
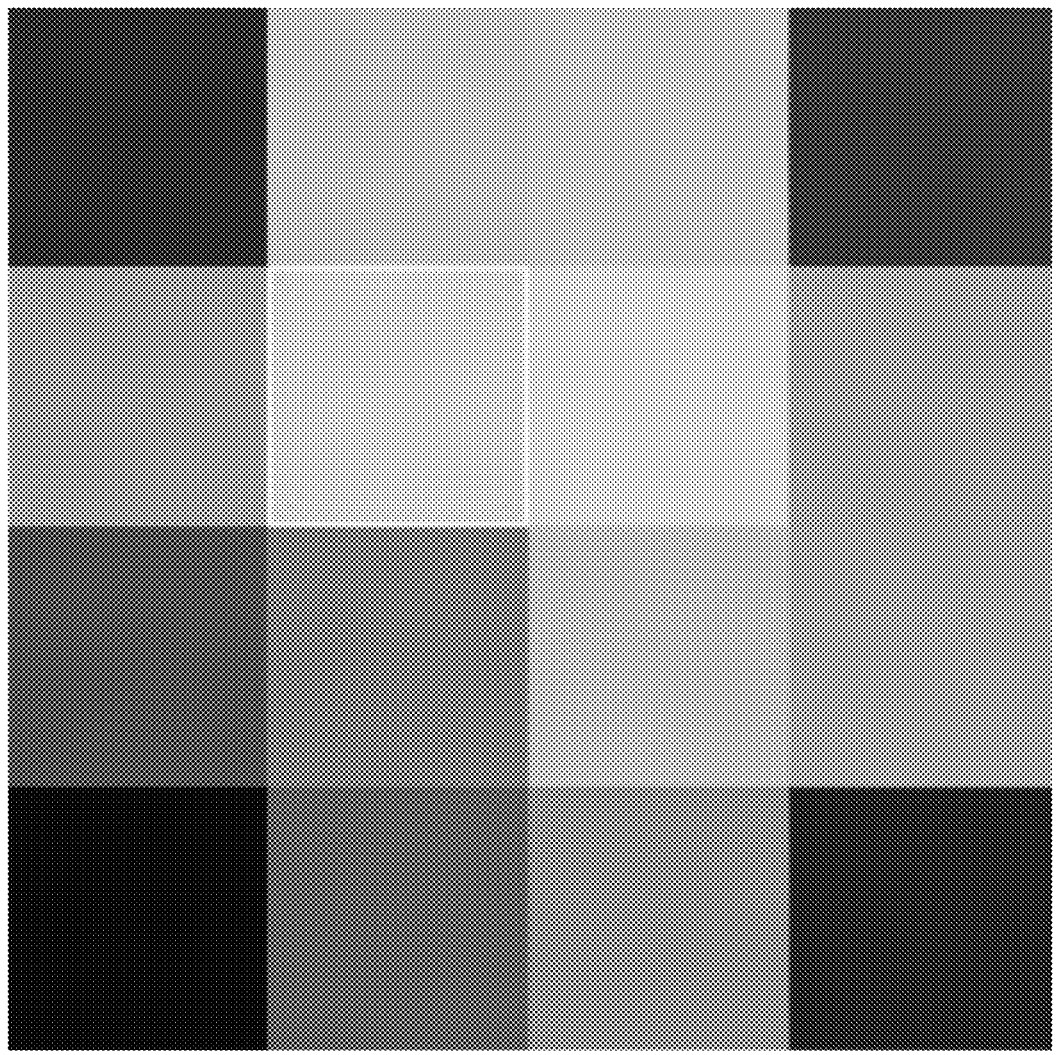
FIG. 2 shows blocks with calculated average value of color saturation.

Reference will now be made in detail to the preferred embodiments of the present invention, examples of which are illustrated in the accompanying drawings.

According to an exemplary embodiment, software for analysis of images from an endoscopic capsule is provided. The endoscopic capsule is swallowed by a patient and then moves down the patient's stomach or the GI tract, transmitting a set of images to an external recorder, that stores the images in its memory. The capsule has an image sensor, for example, CMOS or CCD, with optics for acquiring images controlled by a built-in microcontroller.

After several hours (depending on a particular capsule endoscope used, typically, from 6 to 12 hours), capsule endoscope's battery becomes drained and the reader is provided to a physician, who moves the images from the reader to a PC, where he can use the appropriate software to analyze them.

The present application proposes a set of tools and algorithms for optimizing and automating the analysis of the images transmitted by such a capsule. The set of tools includes:

Removal of repeat frames. Because the endoscope capsule can stay almost motionless for some time (because of an absence of peristaltic contractions to propagate capsule endoscope down in the GI tract), it can collect and transmit a plurality of similar (or the same) images that will take physician's time during the analysis process, without any significant information provided.

A mechanism to detect such frames is as follows. Consider a stream of frames [a1 . . . an], with a degree of similarity between the frames given by d(ai, aj) (the lower the d, the more similar the frames are to each other). The stream is divided into a minimum number of pieces, such that each piece [ak . . . al], d(ak, ai)<D for all i, in other words, so that the frames in that piece are not too different from each other. Only the first frame needs to remain for viewing by the physician. D is selected experimentally, and is typically around 0.5 (roughly in the interval 0.35 to 0.65). D can also change during the viewing the process, and can be adjusted by the user.

Automatic speed adjustment is implemented as follows. Additionally, to decrease the possibility of skipping significant frames, d(ak, ai) can be tied to the video playback speed, so that the speed will increase if d(ak, ai) decreases. Value D can be selected to skip mostly identical frames and speed adjustment during playback can be also implemented to show partly identical frames faster and significantly different frames—slower.

Anomaly detection. Various anomalies can be automatically identified, such as color anomalies, shape anomalies and texture anomalies. Generally, the approach for the different anomalies is similar: a signal x is automatically extracted from the frame via image processing computations, where x corresponds to a set of pixels, for example, representing a share of red pixels in the frame, and then comparing the value of the signal x for normal frames vs. the current frame.

A rule f(ai)→{0,1}, identifies the signal from the frame ai, and determines if the frame is anomalous, or not. The rule itself is constructed based on statistics and machine learning techniques, as is known in image processing art. Using different ways of constructing the signal x, different anomalies can be detected. For color anomalies, x is the histograms for different color channels of the frame. Saturation and hue channels are best used, since they do not depend on the light intensity.

For shape anomalies, x is the value of curvature in different regions of the frame. A two-dimensional Gaussian coefficient is a reasonably good measure of curvature. For texture anomalies, x is the set of numbers [g1 . . . gm], where gi—is the average brightness of the frame with the Gabor filter Gi. Different Gi "encourages" different repeating templates in the image.

The frames can be classified using a machine learning algorithm, such as an SVM support vector machine. The algorithm works as follows: let there be a set of signals for anomalous frames Xa, and a set of signals Xn for normal frames. X is a set of points in a multidimensional space. The algorithm attempts to draw a hyperplane between Xa and Xn that is maximally distant from both.

The images can be displayed simultaneously on the desktop. Removal of repeated or identical frames can also mean removal of nearly identical frames. The measure d(ai, aj) is constructed as follows: for each pair of ai, aj, histograms H(ai) and H(aj) are constructed, where H is the saturation histogram of the frame. The hypothesis of identity or near identity of the frames is tested using Pearson's test:

$$d(H_1, H_2) = \sum_I \frac{(H_1(I) - H_2(I))^2}{H_1(I)}$$

This permits for avoiding spending extra time on images when the capsule is barely moving or moving very slowly. Automatic speed adjustment, as described above, can also use the same principle to identify pieces of the stream with many similar frames.

Identification of color/shape/texture anomalies is based on identifying deviations of pixel parameters from the norm. Frames with anomalies can be marked for further review by the physician. As aids in determining the anomalies, quantiles of the histograms, with RGB channels, can be used, as well as average or Gaussian curvature of the surface of the intestine, and/or Gabor filter spectrograms.

As an option, multiple images can be shown on the desktop simultaneously, in the form of a matrix, in chronological order. Conventional software for capsule endoscope investigation analysis allows viewing several frames simultaneously during the playback, so that a physician with certain skills can analyze more information per unit time, thus decreasing the overall time spent on the investigation.

The concept of an "image matrix" is based on the fact that a human brain does not work with constant speed and concentration even over a short period of time. So the playback should be carefully tied to the activity of the brain. Since there is no robust way of determining the best time to give a new portion of data to the brain, the solution here was to eliminate the conventional "playback" pattern, fill the screen with the images and give a physician an ability to scroll through them on his own.

Additional usability features can also be implemented in this mode. A physician often has the need to perform two separate actions—amplification of the image to get a closer look and marking (annotating) of the image if it has significant information. Since the amplification is performed more often, it is performed on a mouse pointer hovering over the image and image marking is performed on a single click.

The proposed method can be used for image analysis in wireless capsule endoscopy during the polyp examination of the gastrointestinal tract. It is based on the analyses of the curvature of three-dimensional surface to reveal the lumps of the gastrointestinal tract. The proposed method can be explained in two steps: mathematical model and image noise smoothing.

The mathematical model is implemented as follows. The software module that detects the convexity in the pictures of the wireless capsule endoscopy and shows its location in the gastrointestinal tract image uses a color image from the endoscopic capsule that is converted into black and white color scheme. As a result of this operation the image in FIG. 1 can be accepted as the mathematical model of a polyp.

The mathematical model assumes that the polyp is a convex in relation to the surrounding landscape and has a form of a perfect sphere. In its center this sphere has brightness significantly greater than on the periphery. The brighter the pixel, the larger the number to which it corresponds. Then, the brightness value at each image pixel is analyzed. According to these numbers and the analyzed brightness value, the 2D image can be converted into a 3D picture. After this, the procedure recognition of the polyp placement begins. In this case the surface curvature of the 3D image at each pixel is measured. Finally by equation (1), the curvature of the Gaussian at each pixel of the model is calculated.

$$K = \frac{F_{xx} \cdot F_{yy} - F_{xy}^2}{(1 + F_x^2 + F_y^2)^2} \quad (1)$$

In the equation, K is curvature value, $F_x$; $F_{xx}$; $F_y$; $F_{yy}$; $F_{xy}$ are derivatives at the pixel on the corresponding orientation line.

Derivatives are obtained by applying Sobel operator. To calculate the derivative of $F_{xy}$, Sobel operator is applied consistently for the y-axis and x-axis.

After taking the derivatives the curvature of the Gaussian and the average curvature for each pixel of the image are calculated. It is an intrinsic measure of curvature. Its value depends only on how distances are measured on the surface.

Thus, we form two two-dimensional set of lattice points G (Gaussian) and M (Mean) in m×n size m—of pixels in the original picture horizontal plane; n—in vertical plane. Elements of the set of lattice points $G_{(i,j)}$ are the values of the Gaussian curvature at points (i, j). For the set of lattice points M the situation is the same.

From these set of lattice points G and M the set of lattice points P (Polyp Curvature) is formed. The elements of P are defined according to the following formula:

$$P_{(i,j)} = G_{(i,j)} - \min(0; M_{(i,j)}) \quad (2)$$

As a result of this selection the elements that exceed a predetermined level a are obtained. That means that there is a polyp in the original image at the pixel corresponding to this element, where bright pixels in an image would indicate the location of the polyp. This, advantageously, assists in polyp recognition, taking the human factor out of the process.

Image noise smoothing is implemented as follows. In reality, during conversion of the image from color to black and white, a so-called "grain" becomes noticeable. When converting into a three-dimension model, these pixels will become areas with a large difference in height. This affects curvature calculation, and the accuracy of the analysis declines.

In order to prevent this inaccuracy, smoothing (Gaussian Blur) is applied. Gaussian smoothing is used in order to enhance image structures at different scales and to reduce image noise. To smooth the original image, as well as its derivatives, radii of Gauss kernels $r_I$ and $r_{dI}$ were defined experimentally. The coefficients are the following: $r_I=3$, $r_{dI}=27$, $\alpha=0.9$. As a result, smoothed images are obtained that enhance the quality of the analysis.

The proposed method allows for automatic recognition of a presents of polyps in the gastrointestinal tract and determining their locations automatically using software that analyzes images obtained from a gastrointestinal endoscopic capsule. Such method can be used to detect polyps and for faster reading and diagnosis of gastrointestinal disease based on the capsule investigation information.

Note that the software marks the frame "suspicious" or "not suspicious" basing on the above calculations. There are two strategies of how to deal with that information—the software can show a physician only "suspicious" frames for fast on-the-fly analysis, or the physician can watch the suspicious frames in the first order and then move to the rest of the investigation (to pay more attention and concentration to suspicious regions, but also check the frames the software did not define as "suspicious").

According to the exemplary embodiment, two-step recognition of hemorrhage is implemented. The proposed method also permits recognition of bleeding areas of the GI tract, and is divided into two basic steps. The first step separates the video fragments containing signs of hemorrhage from those that do not contain them. The second step includes further analysis of the images of bleeding confirming whether or not the images contain evidence of active hemorrhage.

According to the exemplary embodiment, selection of images without hemorrhage is implemented. In the gastroenterological image, the most definitive evidence of hemorrhage is the presence of bright red or dark red areas. It is important to note that almost in the whole gastrointestinal tract red color is predominating. But red in non-bleeding areas is less intensive than in bleeding. Automatic recognition of bleeding areas can be converted to the recognition of image areas with an intense red color.

Color saturation and its hue can be easily found out by changing the color scheme of the image on the HSV (Hue, Saturation, and Value). As it was mentioned before, most gastroenterological images have red hue. In the intestinal tract the prevailing colors range from orange to yellow-green due to presence of residual of excrements and mucosa chemistry itself. It makes discrimination of hemorrhage more difficult. However, color saturation is almost independent of the capsule location. It is used in the first step of the proposed algorithm of the separation of images that contain hemorrhage from those that do not contain hemorrhage.

To get a primary classification (contains—does not contain) a block approach is used. It offers the possibility to analyze the entire video quickly. Each image is divided into blocks of 64 to 64 pixels, and for each $B_i$ the average value of color saturation is calculated. The blocks at the corners of the image contain very little pixels of our interest and can be regarded as containing no hemorrhage.

Then, the algorithm finds the second unit of saturation of the remaining twelve $B_{2-min}$. Block with the lowest saturation is not considered because it usually corresponds to the lumen of the gastrointestinal tract through which the capsule is moving. The image is recognized as containing the hemorrhage if at least one block that contains blood satisfies the following condition:

Hemorrhage exists if: $I_s(B_i) > I_s(B_{2-min}) + m$, where $I_s$ is the average value of color saturation in the block, m is security border. During testing, it was set at 0.15. In case the image does not correspond to this condition, there is no hemorrhage.

The paler the block is in an image, the brighter color saturation of pixels contained in it is. The block that corresponds to $I_s(B_{2-min})$ is marked by a frame. However, some images that do not contain real signs of hemorrhage may be incorrectly classified as containing bleeding. In the second step, these images are checked and physician should review their status.

Inspection and final determination of hemorrhage is implemented as follows. In the second step, only the endoscopic images that were marked as (potentially) containing the hemorrhage are considered. This step continues the analysis of images and confirms or refutes the solution obtained in the previous step. The pixel analysis of brightness and color saturation is carried out, while the previous step only works with the average values of saturation in large blocks (64×64=4096 pixels in each block).

Hemorrhage in the images with wireless capsule endoscopy usually corresponds to a range of relatively small values of brightness. The primary analysis for training purposes showed that the bleeding areas often contain the values of pixels luminance between 30 and 80. As a result, two-level boundary can be calculated. $T_L$ in the following condition corresponds to the lower boundary, $T_U$—to the top (upper) boundary.

Hemorrhage: $T_U > I(x,y) > T_L$

No hemorrhage: in all other cases.

However, due to the difference in illumination of various areas, making fixed boundaries in endoscopic images is not a good idea. Thus, it is better to set dynamical boundaries. Characteristic $I_{ave}$ is the average value of pixel brightness for each image. It is used for automatic boundary setting.

$T_U = I_{ave} + 10, T_L = I_{ave} - 30.$

The color saturation is also used here but for pixel analysis. It is worth mentioning that for well-lit images, in which red color is dominating, the color saturation can reach very high values. This is the main cause of the second kind of mistakes (omission of hemorrhage in the image that actually contains it) in analysis in the first step. In the second step, the bleeding areas with high saturation are detected due to the following conditions:

Hemorrhage: $0.95 > I_s(x,y) > 0.7$

No hemorrhage: in all other cases. Thus, the hemorrhage determination is, advantageously, made by an automate algorithm. Classification, proposed in the second step, involves a combination of analysis of brightness and saturation. The final decision depends on ration of these results and different lighting conditions. It can be expressed with the following conditions:

$I_{ave} < 60$: Image lacks illumination, therefore, only the analysis of the saturation will be effective.

$I_{ave}$ in range [60,75]: Criteria of brightness and saturation are used in combination. Hemorrhage classification requires coincidence between both criteria.

$I_{ave} > 75$: Criteria of brightness and saturation are used in combination, but due to the fact that the image is too bright, the calculation of SAT (x, y) is now selected in the modified criterion: $0.95 > I_s(x, y) > 0.85$.

Figure 3:
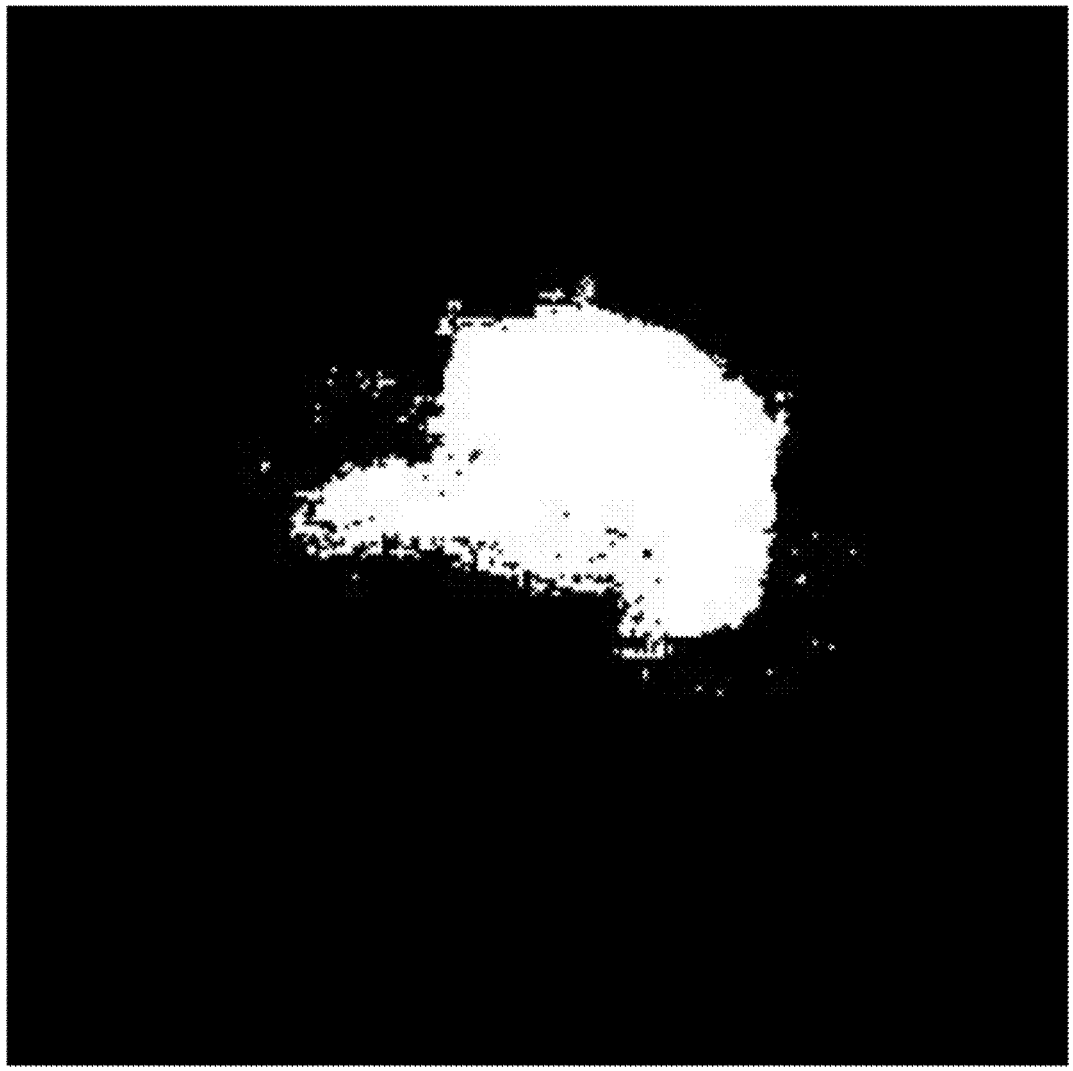
FIG. 3 shows white pixels corresponding to hemorrhage.

In order to make the classification more absolute the image is divided by the levels of the hemorrhage intensity. A four-level classification is used. Each level corresponds to a certain color code (see FIG. 3). For these purposes, the total number of pixels $N_{S2}$ is analyzed. They are marked after the second step as hemorrhage.

$N_{S2}$ is compared with $N_{min}$ (characteristic, used to distinguish images in levels). On default, the value $N_{min}$ is set at 450 if only the criterion of color saturation was used. If both criteria of saturation and brightness are used, this characteristic is set at 5000. The decision about the status of the image with bleeding is made according to the following rules:

Level 0 (no hemorrhage):

$N_{S2} < N_{min}$

Level 1 (hemorrhage of low intensity):

$N_{min} < N_{S2} <= 1.8 N_{min}$

Level 2 (moderate hemorrhage):

$1.8 N_{min} < N_{S2} <= 2.6 N_{min}$

Level 3 (hemorrhage of high intensity):

$N_{s2} > 2.6 N_{Min}$

Identification of the Gastrointestinal Tract Sections in the Wireless Capsule Endoscopy Images. Generally, there are two basic strategies for detecting capsule position inside GI tract based on its approximate location, that can be obtained from motion sensors (accelerometer and/or gyroscope) or on time passed since the capsule was swallowed by a patient (medical research shows that the average time capsule spends in different sections of GI tract is quite similar for different people). Both of these methods have significant disadvantages—motion sensor requires additional space, power and radio channel bandwidth in the capsule endoscope, and time estimation works well for the esophagus and stomach, but shows poor results in further downstream sections of GI tract, especially if certain diseases like polyps or tumors take place. A method of getting the information about the location of the capsule in the gastrointestinal tract based on retrieved images to enable easier examination for physicians is described herein. Identification of key images is performed. The proposed method uses color image analysis obtained in this part of the tract includes two stages.

In the first stage, all the images are converted into the HSV color scheme of (Hue, Saturation, and Value). After that, the normalizing histograms of color saturation are constructed. They are compared to each other, and extra images are removed (that are slightly different from the contiguous).

Using the Pearson's chi-square distribution the histograms are compared. The repeating in succession factors that occur with the lowest frequency are heavier than those that occur with greatest frequency. Analyzing the weight comparing the histograms of contiguous images, we can identify a similarity coefficient of the images. The smaller the coefficient is, the more similar to each other the images are.

For example, two images that have the coefficient of similarity equal to zero are identical. By defining threshold factor $k_S$, we can find out the images that are identified as key. The first image is marked as a key, and each following is compared with it. If the coefficient of similarity k is larger than the threshold $k_S$ we obtain new key image. Next images are compared with it.

Identification of the gastrointestinal tract sections is performed as follows. In the second step after getting the key image the histograms of colour saturation are compared with standard samples of the parts of the gastrointestinal tract. Standard saturations for different parts of the GI tract are obtained based on the key frames. These property templates are used for the future references.

Figure 4:
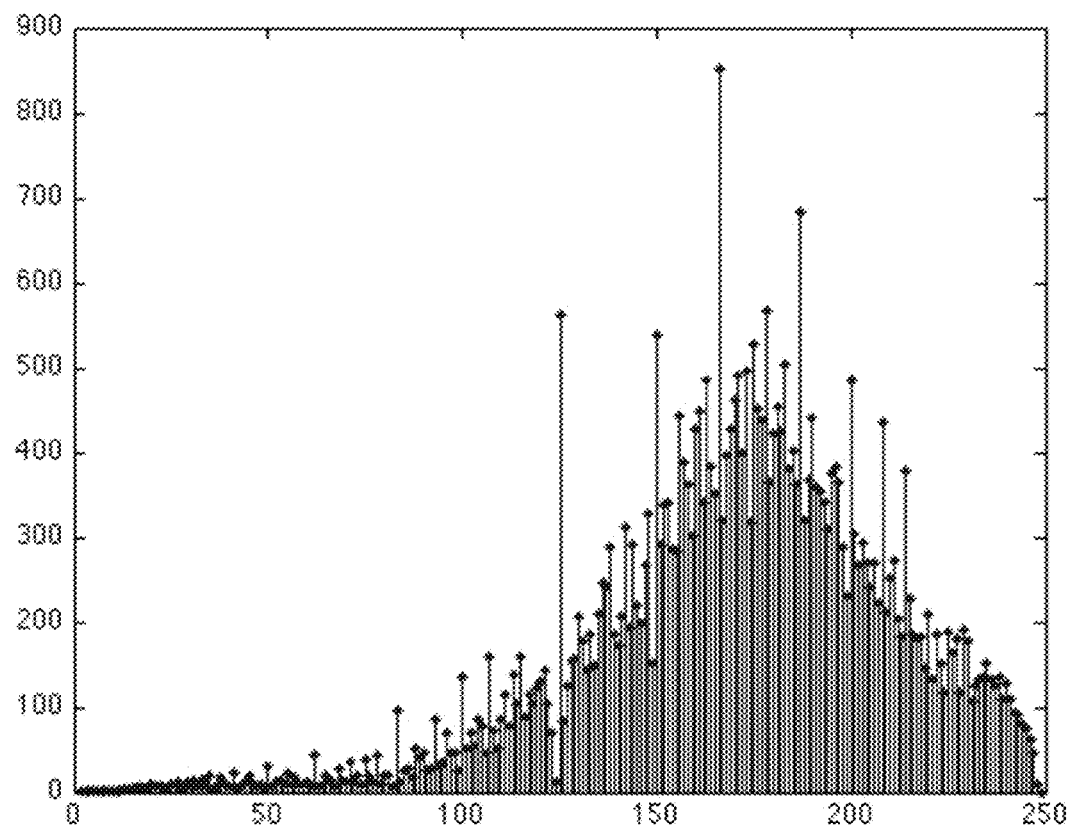
FIG. 4 shows a sample histogram of color saturation of the stomach.
Figure 5:
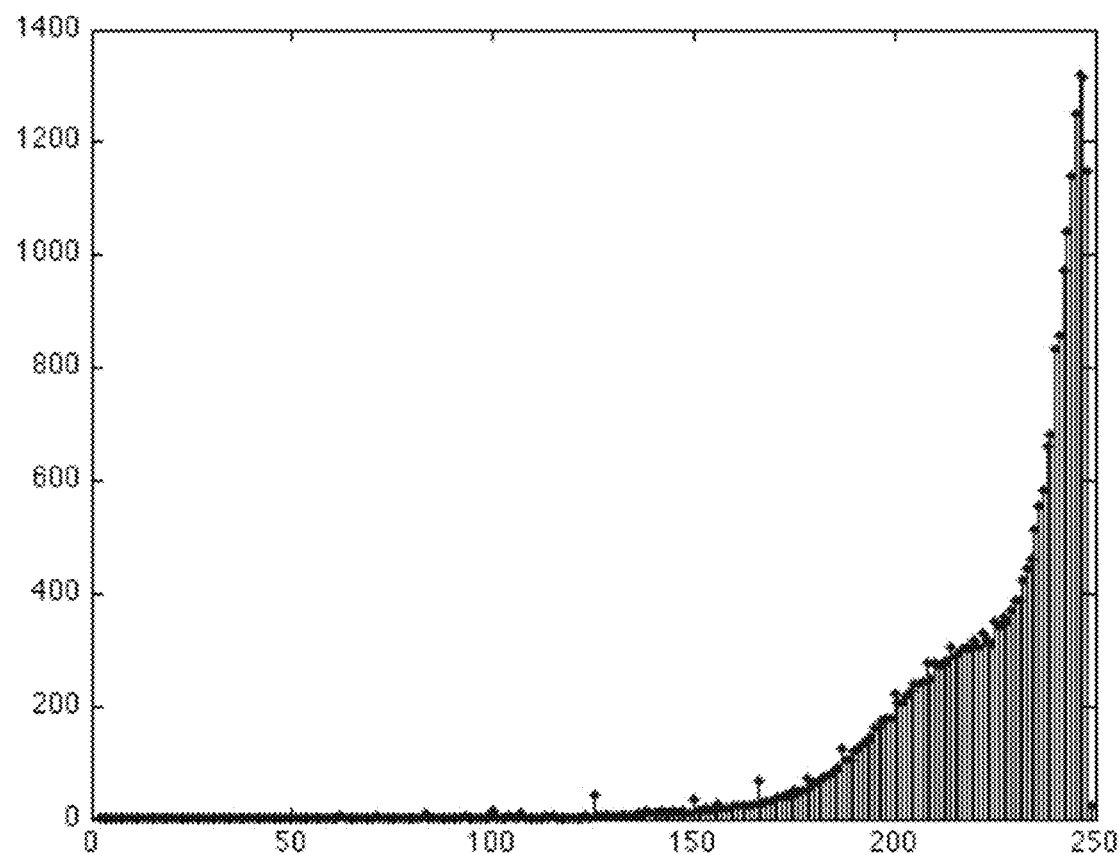
FIG. 5 shows a sample histogram of color saturation of the intestine.

Sample histograms are obtained experimentally by operating the available material from different patients— see FIG. 4 and FIG. 5. In the diagram:

X-axis—the value of saturation;

Y-axis—the number of pixels with a particular saturation.

In practice, while determining the sections of the gastrointestinal tract some "clutter" may appear. The image from the intestine might be recognized as an image from the stomach. That can be avoided in case the program takes into account where the contiguous pictures of the digestive tract section have been taken.

At the same time it is worth remembering the fact that the study begins from the stomach and the capsule is moving only in one direction. With these restrictions the sections of the gastrointestinal tract in the images can be accurately identified. The module associates each image with a section of the gastrointestinal tract from which it was taken. Thus, the processing of data obtained by capsule endoscopy can be greatly simplified by automating the process of image selection suitable for the study.

Figure 6:
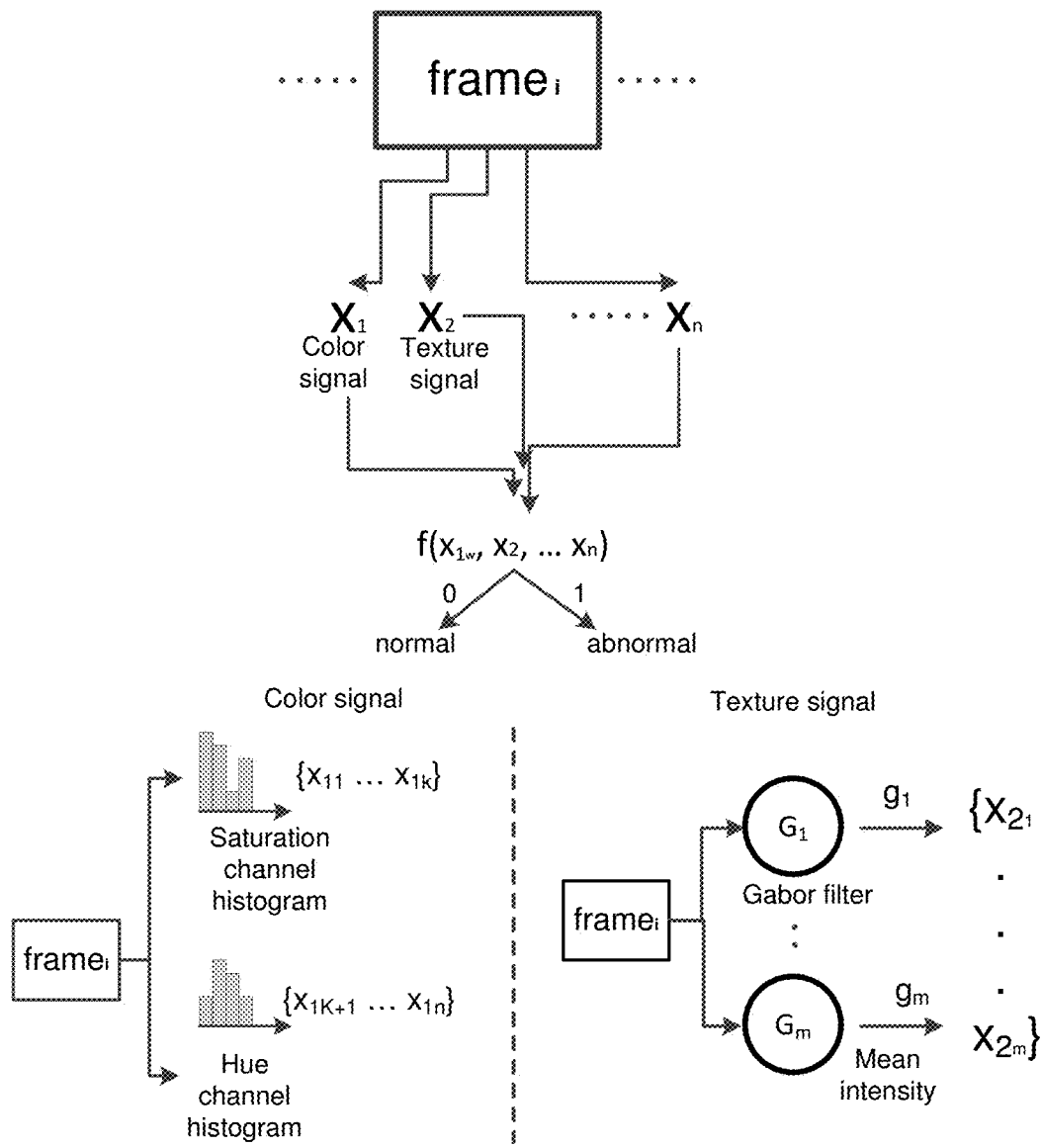
FIG. 6 shows a flow chart of image processing, according to one embodiment of the invention.

FIG. 6 illustrates an image processing method, according to one embodiment of the invention. Color, texture and other signals Xn are extracted from an image frame i and abnormalities are detected in a color signal by using a saturation channel histogram and a hue channel histogram. The abnormalities of the texture signal are detected using an average brightness of the frame with the Gabor filter Gi (see discussion above).

Figure 7:
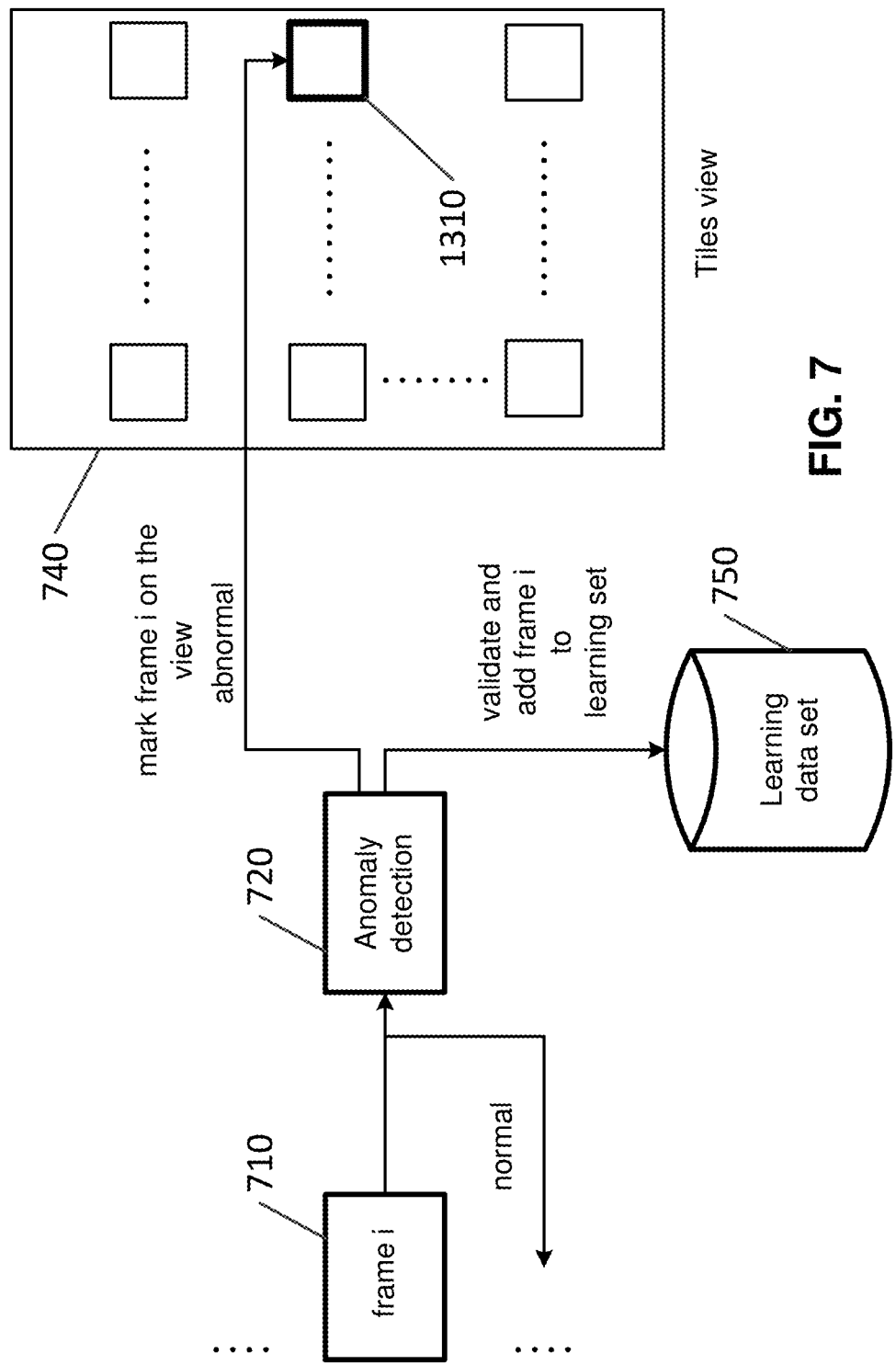
FIG. 7 shows a system block diagram, according to one embodiment of the invention.

FIG. 7 illustrates a system block diagram, according to one embodiment of the invention. An image frame 710 is analyzed for anomalies by module 720. If the anomaly is detected, the frame 710 is marked on a view 740. Then, the frame i is validated and added to a learning (knowledge) data set 750.

According to the exemplary embodiment, the usability of the endoscopic capsule is increased by the following techniques. Routine operations performed by a physician usually take a lot of time during the investigation analysis stage and even more if the entire period of capsule endoscopy analysis software usage is considered. It makes the usability one of the primary concerns in increasing the software solution efficiency.

One of the goals, therefore, is to decrease the amount of mouse clicks/keyboard presses to perform routine operations. To provide the best optimization all general actions have been sorted in the order of usage frequency. The following are the actions sorted by use frequency from the most frequently used ones to the least frequently used ones: play/pause the video, mark "suspicious" frame, open the last investigation for the specific patient, open the last investigation physician was working on.

First and second actions are performed in one click in all conventional software programs. The third step is performed in 4 clicks—open the patients list, select patient, select investigation, open the investigation. This can be changed to "open the patients list, click the patient" (investigation to be opened on a second click will be the last performed with this particular patient).

The fourth action is usually performed in 5 clicks, responsible to login button click, open the patients list, select patient, select the investigation, and open the investigation. This was reduced to 1 click, because the last investigation physician worked on opens right after the login window, when the entity of the physician is established and verified by a login-password pair.

Note that after a couple investigations analyzed, the physicians are used to refer their previous experience to compare the current patient with patients suffering from the similar illness he or she had diagnosed before. It is conventionally done by comparing the paper or electronic reports. To automate this feature, a tag can be added to every frame (marked or unmarked).

All tags, set by a physician, are stored in computer memory in a form of a file or a database. Analyzing a particular frame, physician can enter the tag (that can be, for example, "ulcer") and all images from all physician's investigations that have this particular tag will be shown on the side of the screen to give an example of previously diagnosed images.

Figure 8:
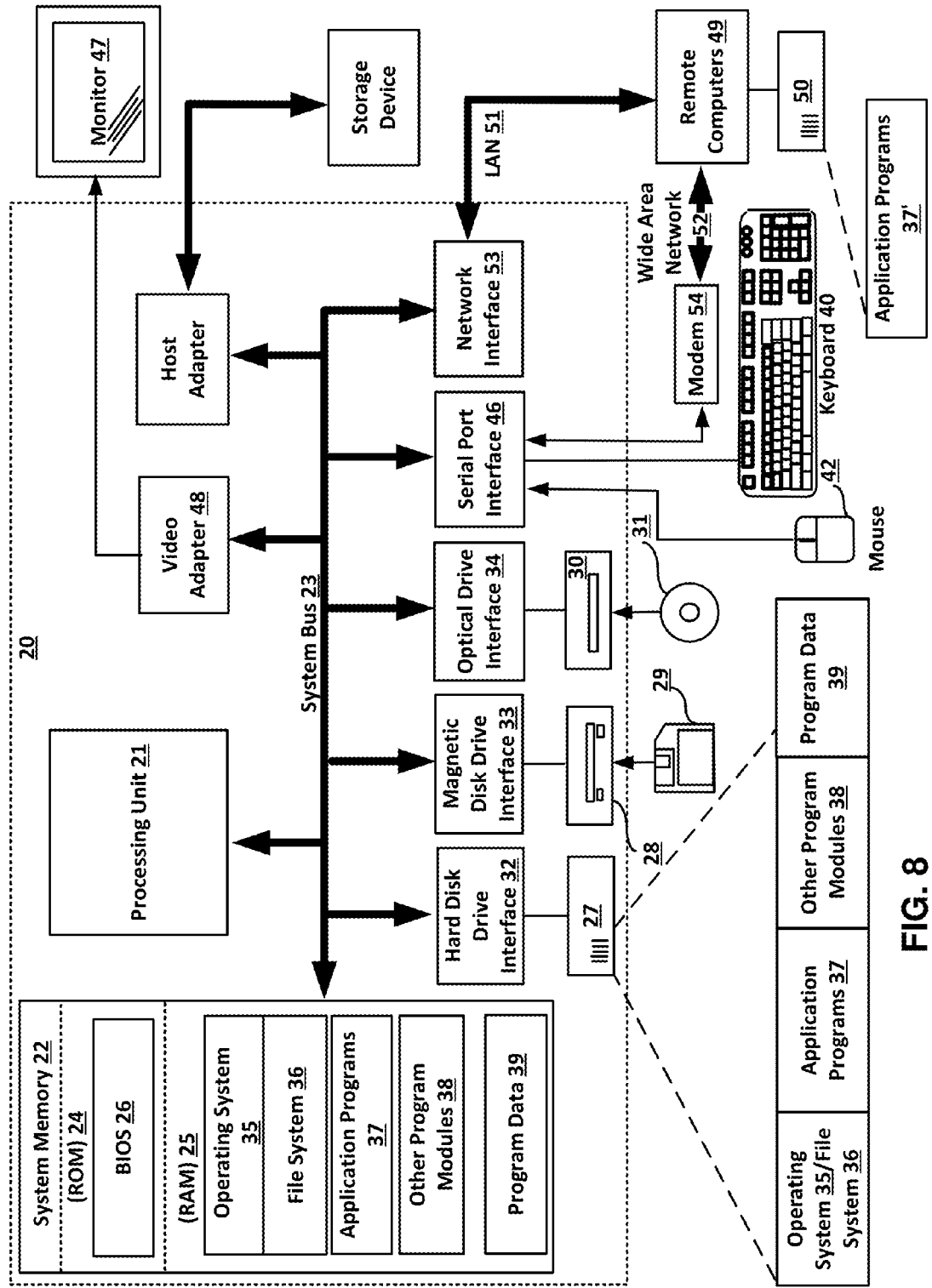
FIG. 8 illustrates a schematic of an exemplary computer system that can be used for implementation of the invention.

With reference to FIG. 8, an exemplary system for implementing the invention includes a general purpose computing device in the form of a computer 20 or a workstation, including a processing unit 21, a system memory 22, and a system bus 23 that couples various system components including the system memory to the processing unit 21.

The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system 26 (BIOS), containing the basic routines that help transfer information between elements within the computer 20, such as during start-up, is stored in ROM 24.

The computer 20 may further include a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD-ROM, DVD-ROM or other optical media. The hard disk drive 27, magnetic disk drive 28, and optical disk drive 30 are connected to the system bus 23 by a hard disk drive interface 32, a magnetic disk drive interface 33, and an optical drive interface 34, respectively. The drives and their associated computer-readable media provide non-volatile storage of computer readable instructions, data structures, program modules and other data for the computer 20.

Although the exemplary environment described herein employs a hard disk, a removable magnetic disk 29 and a removable optical disk 31, it should be appreciated by those skilled in the art that other types of computer readable media that can store data that is accessible by a computer, such as magnetic cassettes, flash memory cards, digital video disks, Bernoulli cartridges, random access memories (RAMs), read-only memories (ROMs) and the like may also be used in the exemplary operating environment.

A number of program modules may be stored on the hard disk, magnetic disk 29, optical disk 31, ROM 24 or RAM 25, including an operating system 35. The computer 20 includes a file system 36 associated with or included within the operating system 35, one or more application programs 37, 37', other program modules 38 and program data 39. A user may enter commands and information into the computer 20 through input devices such as a keyboard 40 and pointing device 42. Other input devices (not shown) may include a microphone, joystick, game pad, satellite dish, scanner or the like.

These and other input devices are often connected to the processing unit 21 through a serial port interface 46 that is coupled to the system bus, but may be connected by other interfaces, such as a parallel port, game port or universal serial bus (USB). A monitor 47 or other type of display device is also connected to the system bus 23 via an interface, such as a video adapter 48. In addition to the monitor 47, personal computers typically include other peripheral output devices (not shown), such as speakers and printers.

The computer 20 may operate in a networked environment using logical connections to one or more remote computers 49. The remote computer (or computers) 49 may be another computer, a server, a router, a network PC, a peer device or other common network node, and typically includes many or all of the elements described above relative to the computer 20, although only a memory storage device 50 has been illustrated. The logical connections include a local area network (LAN) 51 and a wide area network (WAN) 52. Such networking environments are commonplace in offices, enterprise-wide computer networks, Intranets and the Internet.

When used in a LAN networking environment, the computer 20 is connected to the local network 51 through a network interface or adapter 53. When used in a WAN networking environment, the computer 20 typically includes a modem 54 or other means for establishing communications over the wide area network 52, such as the Internet.

The modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing a communications link between the computers may be used.

Having thus described a preferred embodiment, it should be apparent to those skilled in the art that certain advantages of the described method and apparatus have been achieved.

It should also be appreciated that various modifications, adaptations and alternative embodiments thereof may be made within the scope and spirit of the present invention. The invention is further defined by the following claims.

What is claimed is:

1. A system for processing images from an autonomous endoscopic capsule, comprising:
   a processor;
   a memory coupled to the processor;
   an analysis module stored in the memory and executed on the processor, the analysis module configured to:
   detect repeat frames in an incoming video stream;
   remove repeat frames that are similar to each other based on a degree of similarity from the video stream, wherein the degree of similarity is determined using Pearson's test $$d(H_1, H_2) = \sum_I \frac{(H_1(I) - H_2(I))^2}{H_1(I)},$$

wherein H are saturation histogram of the frames;
   adjust a speed of a play back of the video stream based on the degree of similarity between sequential frames;
   detect anomalies by comparing a current frame against a frame or frames without anomalies;
   mark frames with anomalies for further review by a physician; and
   display multiple images on a physician's desktop simultaneously in a chronological order in a form of a matrix.

2. The system of claim 1, wherein the analysis module is configured to adjust the speed of the play back to show frames with a high degree of similarity faster and frames with a low degree of similarity slower.

3. The system of claim 1, wherein the detecting of the anomalies comprises detecting any of:
   color anomalies;
   texture anomalies; and
   shape anomalies.

4. The system of claim 1, wherein the analysis module is configured to remove frames based on a pre-set degree of similarity.

5. The system of claim 1, wherein the analysis module is configured to detect anomalies by extracting a signal x corresponding to a set of x pixels in a frame and comparing a value of the signal x for frames without anomalies against the current frame.

6. The system of claim 5, wherein the signal x is a histogram for different color channels of the frame used for detection of color anomalies.

7. The system of claim 6, wherein the color channels are saturation channels.

8. The system of claim 6, wherein the color channels are hue channels.

9. The system of claim 5, wherein the signal x is a value of a curvature in different regions of the video frame used for detection of shape anomalies.

10. The system of claim 9, wherein a two-dimensional Gaussian coefficient is used for measuring the curvature in the different regions of the video frame.

11. The system of claim 5, wherein the signal x is a set of values representing an average brightness of the frame with the Gabor filter used for detection of the texture anomalies.

12. The system of claim 1, wherein the analysis module is configured to apply Gaussian smoothing to enhance image structures and reduce noise.

13. The system of claim 1, wherein the analysis module is configured to convert the frames into HSV format.

14. The system of claim 1, wherein the analysis module is configured to detect anomalies by any of:
   quintiles of the histograms of RGB channels;
   an average curvature of a surface of an intestine;
   a Gaussian curvature of a surface of an intestine; and
   a Gabor filter spectrogram.

15. A method for processing images from an autonomous endoscopic capsule, the method comprising:
   acquiring a video stream from the endoscopic capsule;
   detecting repeat frames that are similar to each other based on a degree of similarity, wherein the degree of similarity is determined using Pearson's test $$d(H_1, H_2) = \sum_I \frac{(H_1(I) - H_2(I))^2}{H_1(I)},$$

wherein H are saturation histogram of the frames;
   removing repeat frames from the video stream;
   adjusting a speed of play back of the video stream based on the degree of similarity between sequential frames;
   detecting anomalies;
   marking frames with anomalies for further review;
   automatically displaying frames with similar anomalies that were previously found, based on a tag given to an anomaly; and
   displaying multiple images simultaneously in a chronological order in a form of a matrix with manually controlled scrolling.

* * * * *